(12) United States Patent
Iyer

(10) Patent No.: US 12,590,116 B2
(45) Date of Patent: Mar. 31, 2026

(54) METHOD FOR PRODUCING ALLULOSE CRYSTALS

(71) Applicant: Tate & Lyle Solutions USA LLC, Hoffman Estates, IL (US)

(72) Inventor: Krishnan Viswanathan Iyer, Champaign, IL (US)

(73) Assignee: Tate & Lyle Solutions USA LLC, Hoffman Estates, IL (US)

( * ) Notice: Subject to any disclaimer, the term of this patent is extended or adjusted under 35 U.S.C. 154(b) by 317 days.

(21) Appl. No.: 18/202,565

(22) Filed: May 26, 2023

(65) Prior Publication Data

US 2023/0295209 A1    Sep. 21, 2023

Related U.S. Application Data

(60) Continuation-in-part of application No. 18/076,607, filed on Dec. 7, 2022, now Pat. No. 12,264,176, which is a continuation of application No. 17/036,995, filed on Sep. 29, 2020, now Pat. No. 11,548,907, which is a division of application No. 16/341,683, filed as application No. PCT/US2017/058753 on Oct. 27, 2017, now abandoned.

(60) Provisional application No. 62/414,280, filed on Oct. 28, 2016.

(51) Int. Cl.
*C07H 3/02*      (2006.01)
*A23L 27/30*     (2016.01)
*C07H 1/06*      (2006.01)

(52) U.S. Cl.
CPC ............... *C07H 3/02* (2013.01); *A23L 27/33* (2016.08); *C07H 1/06* (2013.01); *C07B 2200/13* (2013.01)

(58) Field of Classification Search
CPC .. C07H 3/02; C07H 1/06; A23L 27/33; C07B 2200/13
USPC ....................................................... 435/105
See application file for complete search history.

(56) References Cited

U.S. PATENT DOCUMENTS

| | | | |
|---|---|---|---|
| 1,708,940 A | 4/1929 | Daly | |
| 2,032,160 A | 2/1936 | Widmer | |
| 2,091,900 A | 8/1937 | Widmer | |
| 2,217,604 A | 10/1940 | Stevens | |
| 2,219,513 A | 10/1940 | Copland | |
| 2,315,699 A | 4/1943 | Goepp, Jr. | |

| | | | |
|---|---|---|---|
| 3,619,293 A | 11/1971 | Nippon | |
| 4,164,429 A | 8/1979 | Mercier | |
| 4,357,172 A | 11/1982 | Edwards | |
| 5,047,088 A | 9/1991 | Liaw | |
| 5,133,807 A | 7/1992 | De Cremoux | |
| 5,195,548 A | 3/1993 | Roger | |
| 5,411,880 A | 5/1995 | Izumori et al. | |
| 6,206,977 B1 | 3/2001 | Heikkila | |
| 6,872,414 B1 | 3/2005 | Myers et al. | |
| 7,838,004 B2 | 11/2010 | Mower | |
| 8,030,035 B2 | 10/2011 | Oh et al. | |
| 8,524,888 B2 * | 9/2013 | Lee .......................... | C07H 1/06 536/127 |
| 8,735,106 B2 | 5/2014 | Hong et al. | |
| 9,144,251 B2 | 9/2015 | Prakash et al. | |
| 10,246,476 B2 | 4/2019 | Kim et al. | |
| 11,291,233 B2 | 4/2022 | Prakash | |
| 11,730,175 B2 | 8/2023 | Meunier | |
| 2004/0258589 A1 | 12/2004 | Golovanoff | |
| 2011/0237790 A1 | 9/2011 | Lee et al. | |
| 2014/0370171 A1 | 12/2014 | Takaoka et al. | |
| 2015/0210996 A1 | 7/2015 | Woodyer et al. | |
| 2017/0313734 A1 | 11/2017 | Kim et al. | |
| 2018/0327796 A1 | 11/2018 | Lee et al. | |
| 2019/0246673 A1 | 8/2019 | Park et al. | |
| 2021/0244057 A1 | 8/2021 | Kim et al. | |
| 2021/0298322 A1 | 9/2021 | Seo et al. | |
| 2022/0079197 A1 | 3/2022 | Bhowmik et al. | |
| 2023/0139835 A1 | 5/2023 | Bachmann et al. | |
| 2023/0172244 A1 | 6/2023 | Zhang | |

FOREIGN PATENT DOCUMENTS

| | | |
|---|---|---|
| AU | 20222386917 A1 | 5/2023 |
| CN | 101109021 A | 1/2008 |
| CN | 102250157 A | 11/2011 |
| CN | 103333935 A | 10/2013 |
| CN | 103540691 A | 7/2015 |
| CN | 115968924 A | 4/2023 |
| DE | 264026 B1 | 5/1990 |
| DE | 4041317 B4 | 9/2005 |
| EP | 0436763 A1 | 7/1991 |
| EP | 2292803 B1 | 2/2013 |
| EP | 3210478 A1 | 8/2017 |
| EP | 2756763 B1 | 12/2017 |
| JP | 05277000 A | 10/1993 |
| JP | 2005006520 A | 1/2005 |
| TW | 201332455 A | 8/2013 |
| WO | 2000056939 A1 | 9/2000 |
| WO | 2011119004 A2 | 9/2011 |

(Continued)

OTHER PUBLICATIONS

Allulose Powder, apuraingredients.com (accessed in Jul. 2025) (Year: 2025).*

(Continued)

*Primary Examiner* — Yih-Horng Shiao
(74) *Attorney, Agent, or Firm* — Matney Legal Group PLLC

(57)          ABSTRACT

Allulose crystals are efficiently produced from an allulose syrup using seed crystals.

26 Claims, 3 Drawing Sheets

(56)                References Cited

FOREIGN PATENT DOCUMENTS

| WO | 2015028784 A1 | 3/2015 |
|----|---------------|--------|
| WO | 2015075473 A1 | 5/2015 |
| WO | 2016012854 A1 | 1/2016 |
| WO | 2016064087 A1 | 4/2016 |
| WO | 2016135458 A1 | 9/2016 |
| WO | 2017029244 A1 | 2/2017 |
| WO | 2022088540 A1 | 5/2022 |
| WO | 2023084114 A1 | 5/2023 |

OTHER PUBLICATIONS

Australian Examination Report for Australian Application No. 2021221889, dated Nov. 17, 2022, 4 pages.
Australian Examination Report for Australian Application No. 2021221893, dated Nov. 17, 2022, 4 pages.
Chinese Office Action for Chinese Application No. 201780066740. 7, dated Aug. 1, 2022, with translation, 19 pages.
International Preliminary Report on Patentability for International Application No. PCT/US2017/058753, dated Apr. 30, 2019, 9 pages.
International Search Report and Written Opinion for International Application No. PCT/US2017/058753, dated May 22, 2018, 15 pages.
Israeli Office Action for Israeli Application No. 289910, dated Aug. 8, 2022, 4 pages.
Japanese Notice of Reasons for Rejection for Japanese Application No. 2019-520948, dated Nov. 16, 2021, with translation, 7 pages.
Taiwanese Office Action for Taiwanese Application No. 106137167, dated Jul. 22, 2021, 9 pages.
A.S. Myerson, Handbook of Industrial Crystallization, 2nd ed. Butterworth Heinemann 2002, pp. 181-184, 295-296.
A.G. Jones, Crystallization Process Systems, Butterworth Heinemann 2002, pp. 44-45, 63-65.
A.-Ch. Eliasson, Carbohydrates in Food, 2nd ed. Taylor & Francis 2006, pp. 60-62.
V.A. Vaclavik et al., Essentials of Food Science, 3rd ed. Springer 2008, pp. 343-344.
L. Rozsa, International Sugar Journal, 2008, 110 (1320).
H. Panda, Sugarcane Processing and By-Products of Molasses, Asia PacificBusiness Press, 2011, pp. 327-329.
J. Sedzik et al., Molecules: Nucleation, Aggregation and Crystallization—BeyondMedical and Other Implications, World Scientific, 2009, 150-167.

Th. Varzakas et al., Food Engineering Handbook—Food Process Engineering, CRC Press 2015, pp. 164-167.
R.R. McKeown et al., Crystallization Design and Scale-up; in D.J. am Ende, Chemical Engineering in the Pharmaceutical Industry—R&D to Manufacturing, Wiley 2011, pp. 213-247.
J. Kraus et al., Zuckerind, 119 (1994) 5, pp. 407-413.
A. Markande et al. Food and Bioproducts Processing 90 (2012) 406-412.
A.E. Lewis et al., Industrial Crystallization—Fundamentals and Applications, Cambridge University Press 2015, pp. 89-91.
A.V. Delgado et al., Sugar processing and by-products of the sugar industry, FAQ Agricultural Services Bulletin 144, 2001, pp. 15-17.
M. Walter et al. 2009, Zuckerindustrie 134 (2009) 12 747-749.
BMA—technik programm, Kristallisationsanlagen, Oct. 2005 and machine translation.
J.C.P. Chen et al., Cane Sugar Handbook, 12th ed., Wiley 1993, pp. 274-276.
The Amylase Research society of Japan, Handbook of Amylases and Related Enzymes, Pergamon Press 1988, pp. 201.
K. Urbaniec, modern energy economy in beet sugar factories, Elsevier 1989, pp. 163-168.
D. Ruytings, Zuckerindustrie 130 (2005) 11 821-826.
B. Elvers, Ullman's Food and Feed, Wiley-VCH 2017, pp. 955-967.
English computer translation of CN 103 540 691 A, (2015).
W. Beckmann, Crystallization—Basic Concepts and Industrial Applications, Wiley-VCH 2013, 260-262.
Office Action for Mexican Patent Application No. MX/a/2019/ 004164, with English translation mailed Jun. 27, 2024, 12 pages.
Third Party Observations in European Patent Application No. 23178268.1, filed Jan. 4, 2024, 19 pages.
Nabors, "Alternative Sweetners," 4th ed, CRC Press, 2012, 4 pages.
Information Statement filed in Japanese Application No. 2022-162448, dated Mar. 25, 2024 with translation, 2 pages.
Office Action for Chinese Patent Application No. 202410161687.0 mailed Jul. 17, 2024, 7 pages.
Minutes and Outcome of Opposition to EP3532481 dated Aug. 11, 2024-Oct. 30, 2025 (83 pages).
Proprietor Communications in Opposition to EP3532481 dated Mar. 9, 2024-Aug. 8, 2025 (156 pages).
Opposer Communications in Opposition to EP3532481 dated Mar. 14, 2024-Aug. 6, 2025 (106 pages).
Mullin, "Crystallization," Fourth Edition, pp. 196-200; 2001 (7 pages).

* cited by examiner

METHOD FOR PRODUCING ALLULOSE CRYSTALS

CROSS-REFERENCE TO RELATED APPLICATION

This application is a continuation-in-part of U.S. application Ser. No. 18/076,607 filed on Dec. 7, 2022, which is a continuation of U.S. application Ser. No. 17/036,995 filed on Sep. 29, 2020 now U.S. Pat. No. 11,548,907, which is continuation of U.S. application Ser. No. 16/341,683, which claims priority to U.S. Provisional Application No. 62/414,280, filed Oct. 28, 2016, the entire disclosures of each of which are incorporated herein by reference for all purposes.

FIELD OF THE INVENTION

The present invention relates to the production of crystals of allulose from syrups containing allulose.

DISCUSSION OF THE RELATED ART

Many food and beverage products contain nutritive sweeteners such as sucrose (generally referred to as 'sugar' or 'table sugar'), glucose, fructose, corn syrup, high fructose corn syrup and the like. Although desirable in terms of taste and functional properties, excess intake of nutritive sweeteners, such as sucrose, has long been associated with an increase in diet-related health issues, such as obesity, heart disease, metabolic disorders and dental problems. This worrying trend has caused consumers to become increasingly aware of the importance of adopting a healthier lifestyle and reducing the level of nutritive sweeteners in their diet.

In recent years, there has been a movement towards the development of replacements for nutritive sweeteners, with a particular focus on the development of low or zero-calorie sweeteners. One proposed alternative to nutritive sweeteners is allulose (also known as D-psicose). Allulose is known as a "rare sugar", since it occurs in nature in only very small amounts. It is about 70% as sweet as sucrose, but provides only around 5% of the calories of sucrose (approximately 0.2 kcal/g). It may therefore essentially be considered to be a 'zero calorie' sweetener.

In view of its scarcity in nature, production of allulose relies on the epimerization of readily available fructose. Ketose-3-epimerases can interconvert fructose and allulose, and various ketose-3-epimerases are known for carrying out this conversion. Such epimerization reactions are typically conducted using an aqueous medium in which fructose is initially dissolved, wherein the allulose-containing product obtained as a result of the epimerization is in the form of a solution of allulose in water. Further processing and purification of the reaction product may be conducted in accordance in known procedures, whereby an allulose syrup containing allulose in fairly high concentration and purity is produced. Such allulose syrups are capable of being used in many consumable products, including foods and beverages, as substitutes for conventional "sugar" syrups such as glucose syrups, high fructose corn syrups and the like.

For other applications, however, it would be desirable to utilize allulose which is in "dry," free-flowing, crystalline form, i.e., a form generally resembling that of table sugar. Although some attempts to develop procedures for producing crystalline allulose have been reported (see, for example, U.S. Pat. No. 8,524,888 and WO 2016/064087), it is generally recognized that allulose is a saccharide which is challenging to crystallize in a controlled, efficient way such that crystals of suitable shape and size are reliably obtained in high yield. Therefore, improved crystallization methods for allulose are still of great interest.

SUMMARY OF THE INVENTION

Various aspects of the present invention may be summarized as follows:

Aspect 1: A method for producing allulose crystals, wherein the method comprises:

a) cooling and agitating a first admixture comprised of a first portion of allulose syrup and allulose seed crystals and initiating crystallization of allulose dissolved in the allulose syrup, thereby forming a first massecuite comprising allulose crystals and a first mother liquor containing residual dissolved allulose, the cooling and agitating being continued until a first preselected target yield of allulose crystals is achieved;

b) optionally, separating the first massecuite into a first portion (which may be subjected to further processing steps, such as separating the allulose crystals from the mother liquor portion and washing and/or drying the separated allulose crystals) and a second portion;

c) optionally, combining a second portion of allulose syrup with the second portion of the first massecuite to form a second admixture; and d) optionally, cooling and agitating the second admixture and initiating crystallization of allulose dissolved in the second portion of allulose syrup, thereby forming a second massecuite comprising allulose crystals and a second mother liquor containing residual dissolved allulose, the cooling and agitating being continued until a second preselected target yield of allulose crystals is achieved.

In various embodiments of Aspect 1, at least steps a) and b) are performed, at least steps a)-c) are performed, or at least steps a)-d) are performed.

Aspect 2: The method of Aspect 1, wherein the first admixture is obtained by combining the first portion of allulose syrup and dry allulose crystals.

Aspect 3: The method of Aspect 1, wherein the first admixture is obtained by combining with the first portion of allulose syrup and a heel comprised of allulose crystals and a mother liquor.

Aspect 4: The method of any of Aspects 1-3, wherein the first admixture and second admixture are agitated in steps a) and d), if step d) is performed, respectively using an agitator having a tip speed of 0.02 to 2 m/sec.

Aspect 5: The method of any of Aspects 1-4, wherein step a) additionally comprises, following initiation of crystallization of allulose dissolved in the allulose syrup, combining at least one additional portion of allulose syrup with the first admixture.

Aspect 6: The method of any of Aspects 1-5, wherein the cooling in step a) involves lowering the temperature of the first admixture from within an initial temperature range to within a second temperature range and holding the temperature of the first admixture within the second temperature range for a period of time.

Aspect 7: The method of any of Aspects 1-6, wherein step d) is performed and the cooling in step d) involves lowering the temperature of the second admixture from within an initial temperature range to within a second temperature range and holding the temperature of the second admixture within the second temperature range for a period of time.

Aspect 8: The method of any of Aspects 1-7, wherein the allulose syrup has a dry solids content of 70% to 95% by weight, 75% to 90% by weight, or 80% to 85% by weight.

Aspect 9: The method of any of Aspects 1-8, wherein the allulose syrup has an allulose purity of at least 70%, at least 75%, at least 80%, at least 85%, or at least 90%.

Aspect 10: The method of any of Aspects 1-9, comprising an additional step of separating allulose crystals from the first mother liquor in the first portion of the first massecuite.

Aspect 11: The method of Aspect 10, wherein the separating is carried out at least in part by one or more physical separation methods selected from the group consisting of centrifugation, filtration, decantation, membrane separation and combinations thereof.

Aspect 12: The method of Aspect 10 or 11, wherein allulose crystals separated from the first mother liquor are subjected to i) washing with at least one of water, an organic solvent, a blend of organic solvents, a blend of water and organic solvent(s) or an aqueous solution comprised of at least one carbohydrate (e.g., allulose); ii) drying; or a combination thereof.

Aspect 13: The method of any of Aspects 1-12, wherein steps b)-d) are performed and repeated at least once.

Aspect 14: A method for producing allulose crystals, wherein the method comprises:

a). passing a feed syrup/recycled massecuite admixture, comprised of i) a feed syrup, comprising water and dissolved allulose, and ii) a recycled massecuite comprising allulose crystals and a recycled massecuite mother liquor containing dissolved allulose, wherein the feed syrup/recycled massecuite admixture has been cooled to within a first crystallization temperature range, through a first stage crystallization zone, while agitating the feed syrup/recycled massecuite admixture, maintaining the feed syrup/recycled massecuite admixture within the first crystallization temperature range and initiating crystallization of allulose dissolved in the feed syrup and recycled massecuite mother liquor, thereby forming a first massecuite comprising allulose crystals and a first mother liquor containing residual dissolved allulose, and withdrawing the first massecuite which has achieved a first preselected target yield from the first stage crystallization zone;

b). optionally, cooling the first massecuite withdrawn from the first stage crystallization zone to within a second crystallization temperature range and transferring the first massecuite to a second stage crystallization zone;

c). optionally, passing the first massecuite through the second stage crystallization zone while agitating the first massecuite, maintaining the first massecuite within the second crystallization temperature range and initiating crystallization of allulose dissolved in the first mother liquor, thereby forming a second massecuite comprising allulose crystals and a second mother liquor containing residual dissolved allulose, and withdrawing the second massecuite which has achieved a second preselected target yield from the second stage crystallization zone; and d). optionally, repeating steps b and c at least once to yield a final massecuite comprising allulose crystals and a final mother liquor.

In various embodiments of Aspect 14, at least steps a) and b) are performed, at least steps a)-c) are performed, or at least steps a)-d) are performed.

Aspect 15: The method of Aspect 14, wherein steps a)-d) are performed and comprising an additional step of separating the allulose crystals in at least a portion of the final massecuite from the final mother liquor.

Aspect 16: The method of Aspect 14 or 15, wherein steps a)-d) are performed and a portion of the final massecuite is used as the recycled massecuite.

Aspect 17: The method of any of Aspects 14-16, wherein the feed syrup/recycled massecuite admixture is obtained by mixing in a mixing vessel the feed syrup with the recycled massecuite comprised of allulose crystals and a recycled massecuite mother liquor containing dissolved allulose to provide the feed syrup/recycled massecuite admixture and transferring the feed syrup/recycled massecuite admixture from the mixing vessel into the first stage crystallization zone.

Aspect 18: The method of any of Aspects 14-17, wherein the first admixture and second admixture are agitated in steps a) and c), if step c) is performed, respectively using an agitator having a tip speed of 0.02 to 2 m/sec.

Aspect 19: The method of any of Aspects 14-18, wherein the allulose syrup has a dry solids content of 70% to 95% by weight, 75% to 90% by weight, or 80% to 85% by weight.

Aspect 20: The method of any of Aspects 14-19, wherein the allulose syrup has an allulose purity of at least 70%, at least 75%, at least 80%, at least 85%, or at least 90%.

Aspect 21: The method of Aspect 15, wherein the separating is carried out at least in part by one or more physical separation methods selected from the group consisting of centrifugation, filtration, decantation, membrane separation and combinations thereof.

Aspect 22: The method of Aspect 15 or 21, wherein allulose crystals separated from the final mother liquor are subjected to i) washing with at least one of water, an organic solvent, a blend of organic solvents, a blend of water and organic solvent(s) or an aqueous solution comprised of at least one carbohydrate (e.g., allulose); ii) drying; or a combination thereof.

Aspect 23: The method of any of Aspects 14-22, wherein the feed syrup/recycled massecuite admixture is passed through the first stage crystallization zone in a plug flow manner and/or, if steps b) and c) are performed, the first massecuite is passed through the second stage crystallization zone in a plug flow manner.

Aspect 24: The method of any of Aspects 1-23, wherein the method is performed in a continuous manner.

Aspect 25: Allulose crystals, obtained in accordance with the method of any of Aspects 1-24.

Aspect 26: A consumable product, comprised of or prepared using allulose crystals in accordance with Aspect 25 and at least one additional ingredient other than allulose crystals.

Aspect 27: A method of making a consumable product, comprising using allulose crystals in accordance with Aspect 25.

Aspect 28: A mother liquor, obtained in accordance with the method of any of Aspects 1-24.

Aspect 29: The mother liquor of Aspect 28, wherein the mother liquor is suitable for use as a product consumable by humans or animals or as an ingredient in a formulated product consumable by humans or animals.

Aspect 30: A method for producing allulose crystals, wherein the method comprises:

a) evaporating a feed allulose syrup at a first sub-ambient pressure and a first temperature to produce a first supersaturated allulose syrup having an allulose syrup target saturation;

b) introducing seed crystals to the first supersaturated allulose syrup and allowing the allulose to crystallize to produce a first massecuite comprising allulose crystals and a first supersaturated mother liquor having a first target mother liquor saturation higher than the allulose syrup target saturation;

c) evaporating the first massecuite at the first sub-ambient pressure and the first temperature to produce a second massecuite comprising allulose crystals and a second supersaturated mother liquor having a second mother liquor target saturation lower than the first mother liquor target saturation;

d) increasing the first sub-ambient pressure to a second sub-ambient pressure and cooling the second massecuite to a second temperature to produce a third massecuite comprising allulose crystals and a third supersaturated mother liquor having a third mother liquor target saturation;

e) holding the third massecuite at the second sub-ambient pressure and the second temperature for a period of time to produce a fourth massecuite comprising fourth allulose crystals and a fourth mother liquor having a fourth target mother liquor saturation;

f) increasing the pressure to ambient and cooling the fourth massecuite to a third temperature at a cooling rate to produce a fifth massecuite comprising fifth allulose crystals and a fifth supersaturated mother liquor having a fifth target mother liquor saturation;

g) allowing the fifth massecuite to crystallize for a crystallization time to produce a product massecuite comprising product allulose crystals at a target yield and a product mother liquor, the product mother liquor having a target product mother liquor supersaturation; and h) separating the product allulose crystals from the product supersaturated mother liquor to provide allulose crystals at the target yield.

Aspect 31: The method of Aspect 30, wherein the target yield is 40% or more.

Aspect 32: The method of Aspect 30 or Aspect 31, wherein the feed allulose syrup has a total dry solids content of from 50% to 80% by weight.

Aspect 33: The method of any of Aspects 30-32, wherein the allulose in the feed allulose syrup is at least 80% pure on a dry solids basis by weight.

Aspect 34: The method any of Aspects 30-33, wherein the pH of the feed allulose syrup is from 2.5 to 6.0.

Aspect 35: The method of any of Aspects 30-34, wherein the feed allulose syrup is at least 95% pure on a dry solids basis by weight.

Aspect 36: The method of any of Aspects 30-35, wherein the feed allulose syrup is at least 98% pure on a dry solids basis by weight.

Aspect 37: The method of any of Aspects 30-36, wherein the seed crystals comprise from 0.0001% to 5% by weight of the feed allulose syrup.

Aspect 38: The method of any of Aspects 30-37, wherein the seed crystals have an average particle size of 75 microns or less.

Aspect 39: The method of any of Aspects 30-38, wherein the seed crystals have an average particle size of from 5 to 250 microns.

Aspect 40: The method of any of Aspects 30-39, wherein the first temperature is from 35 to 50° C.

Aspect 41: The method of any of Aspects 30-40, wherein the first target mother liquor saturation is from 1.10 to 1.15.

Aspect 42: The method of any of Aspects 30-41, wherein the first supersaturated mother liquor comprises from 85-90 wt % allulose on a dry solids basis.

Aspect 43: The method of any of Aspects 30-42, wherein the second temperature is from 22 to 35° C.

Aspect 44: The method of any of Aspects 30-43 wherein the second target mother liquor saturation is 1.05 supersaturated or less.

Aspect 45: The method of any of Aspects 30-44, wherein the second supersaturated mother liquor comprises from 80 to 95 wt % allulose on a dry solids basis.

Aspect 46: The method of any of Aspects 30-45, wherein the third temperature is from 20 to 25° C.

Aspect 47: The method of any of Aspects 30-46, wherein the third target mother liquor saturation is from 1.1 to 1.2 supersaturated.

Aspect 48: The method of any of Aspects 30-47, wherein the fourth target mother liquor saturation is from 1.05 to 1.2 supersaturated.

Aspect 49: The method of any of Aspects 30-48, wherein the separating is carried out at least in part by one or more physical separation methods selected from the group consisting of centrifugation, filtration, decantation, membrane separation and combinations thereof.

Aspect 50: The method of any of Aspects 30-49, wherein allulose crystals separated from the final mother liquor are subjected to i) washing with at least one of water, an organic solvent, a blend of organic solvents, a blend of water and organic solvent(s) or an aqueous solution comprised of at least one carbohydrate; ii) drying; or a combination thereof.

Aspect 51: Allulose crystals, obtained in accordance with the method of any of Aspects 30-50.

Aspect 52: A consumable product, comprised of or prepared using allulose crystals in accordance with any of Aspects 30-51 and at least one additional ingredient other than allulose crystals.

Aspect 53: A method of making a consumable product, comprising using allulose crystals in accordance with any of Aspects 30-51.

Aspect 54: A mother liquor, wherein the mother liquor is the product mother liquor obtained in accordance with the method of any of Aspects 30-53.

Aspect 55: A mother liquor, wherein the mother liquor is the product mother liquor obtained in accordance with the method of any of Aspects 30-54 and wherein the mother liquor is suitable for use as a product consumable by humans or animals or as an ingredient in a formulated product consumable by humans or animals.

DETAILED DESCRIPTION OF CERTAIN EMBODIMENTS OF THE INVENTION

Feed Allulose Syrup

Figure 1:
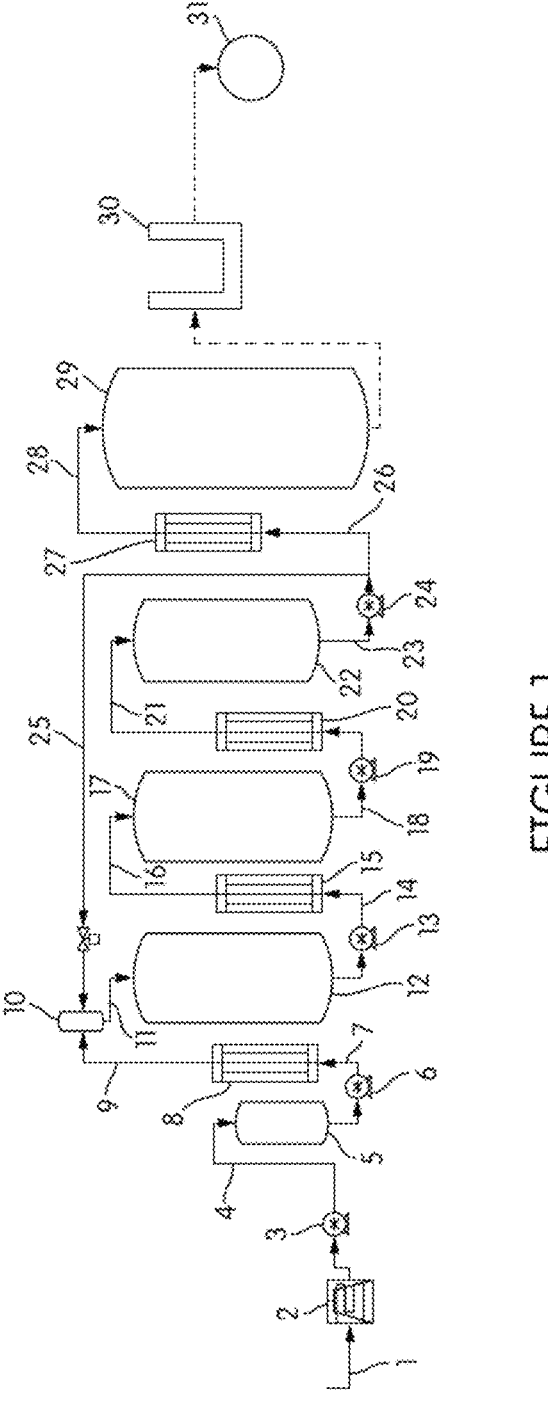
FIG. 1 illustrates in schematic form a crystallization system and process in accordance with one embodiment of the invention.

The present invention utilizes at least one allulose syrup as a starting material, i.e., a feed allulose syrup for a crystallization process, wherein allulose present in dissolved form in the feed syrup is converted to crystalline form. Methods of obtaining allulose syrups are well known in the art and are described, for example, in the following patent documents, the disclosure of each of which is incorporated herein by reference in its entirety for all purposes: WO 2016/135458; US 2015/0210996; U.S. Pat. Nos. 5,411,880; 8,735,106; 8,030,035; and 11,653,688.

For example, the feed allulose syrup may be prepared by a process comprising contacting an aqueous solution of fructose with an allulose (D-psicose) epimerase enzyme under conditions effective to convert at least a portion of the fructose to allulose, purifying the reaction product obtained, and then concentrating the purified reaction product to a desired dry solids content. The purification steps may involve the removal of impurities from the reaction product using one or more techniques such as deproteination, decolorization (treatment with decolorizing agent(s)), desalting, ion exchange chromatography (using one or more ion exchange resins, such as anion exchange resin, cation exchange resin and the like), column chromatography, fractionation, and the like.

The feed allulose syrup should have a dry solids content which is sufficient to effect crystallization of allulose when the feed syrup is cooled in the presence of seed crystals, as described hereafter in more detail. For example, in various embodiments, the dry solids content of the feed allulose syrup may be at least 50% by weight, at least 55% by weight, at least 60% by weight, at least 65% by weight, at least 70% by weight, at least 75% by weight, at least 80%, or at least 85% by weight by weight. However, it will generally be preferred that the dry solids content of the allulose be sufficiently low that the feed syrup remains a free-flowing solution in the absence of seed crystals at the temperature at which the syrup is to be maintained prior to the initiation of crystallization by the introduction of seed crystals. Thus, in various embodiments of the invention, the feed allulose syrup has a dry solids content not greater than 90% or not greater than 85%. The desired dry solids content may be attained by subjecting a diluted allulose solution to an evaporation or concentration procedure wherein volatiles (e.g., water) are removed from the solution, leaving behind a more concentrated syrup. The evaporation/condensation conditions may advantageously be selected so as to minimize or reduce the extent of allulose degradation; for example, relatively low evaporation temperatures may be employed.

According to some embodiments, the allulose feed syrup has a total dry solids content of from 50% to 80% by weight, and comprising allulose in an amount of at least 80% by weight on a dry solids basis, wherein the pH of the feed syrup is from 2.5 to 6.0.

According to another embodiment, the feed allulose syrup has a total dry solids content of from 70% to 80% by weight, and comprises allulose in an amount of at least 90% by weight on a dry solids basis, wherein the pH of the syrup is from 3.0 to 5.0.

The total dry solids content of the feed allulose syrup is from 50% to 80% by weight. For example, the total dry solids content may be 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% or 80% by weight, as well as all intermediate values.

In an embodiment, the total dry solids content of the feed allulose syrup is from 70% to 80% by weight. For example, the total dry solids content may be 70%, 71%, 72%, 73%, 74%, 75%, 76%, 77%, 78%, 79% or 80% by weight, as well as all intermediate values. In an embodiment, the total dry solids content of the feed allulose syrup is from 71% to 78% by weight. In another embodiment, the total dry solids content of the feed allulose syrup is from 71% to 73% by weight. In another embodiment, the total dry solids content of the feed allulose syrup is from 76% to 78% by weight. In another embodiment, the total dry solids content of the feed allulose syrup is from 50% to 70% by weight.

The pH of the feed allulose syrup is from 2.5 to 6.0. For example, the pH of the syrup may be 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 or 6.0, as well as all intermediate values.

In an embodiment, the pH of the feed allulose syrup is from 3.0 to 5.0. For example, the pH of the syrup may be 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 as well as all intermediate values. In an embodiment, the pH of the feed allulose syrup is from 3.5 to 4.5. For example, the pH of the syrup may be 3.5, 3.6, 3.7, 3.8, 3.9, 4.0, 4.1, 4.2, 4.3, 4.4 or 4.5 as well as all intermediate values. In an embodiment, the pH of the feed allulose syrup is from 3.8 to 4.2. In an embodiment, the pH of the feed allulose syrup is about 4.0. The feed allulose syrup comprises allulose in an amount of at least 80% by weight on a dry solids basis (i.e., of the total dry solids present in the feed allulose syrup, at least 80% by weight is allulose). For example, the feed allulose syrup may comprise allulose in an amount of 80%, 81%, 82%, 83%, 84%, 85%, 86%, 87%, 88%, 89%, 90%, 91%, 92%, 93%, 94%, 95%, 96%, 97%, 98%, 99% or 100% by weight on a dry solids basis, as well as all intermediate values.

In an embodiment, the feed allulose syrup comprises allulose in an amount of at least 90% by weight on a dry solids basis (i.e., of the total dry solids present in the feed allulose syrup, at least 90% by weight is allulose). For example, the allulose syrup may comprise allulose in an amount of 90%, 91%, 92%, 93%, 94%, 95%, 96%, 97%, 98%, 99% or 100% by weight on a dry solids basis, as well as all intermediate values. In an embodiment, the feed allulose syrup comprises allulose in an amount of at least 95% by weight on a dry solids basis. In an embodiment, the feed allulose syrup comprises less than 1000 ppm of HMF (hydroxymethylfurfural). For example, the feed allulose syrup may comprise less than 900 ppm, less than 800 ppm, less than 700 ppm, less than 600 ppm, less than 500 ppm, less than 400 ppm, less than 300 ppm, less than 200 ppm or less than 100 ppm of HMF. In certain embodiments, the allulose syrup comprises more than 0.1 ppm and less than 1000 ppm of HMF (hydroxymethylfurfural), for example more than 0.1 ppm and less than 900 ppm, more than 0.1 ppm and less than 800 ppm, more than 0.1 ppm and less than 700 ppm, more than 0.1 ppm and less than 600 ppm, more than 0.1 ppm and less than 500 ppm, more than 0.1 ppm and less than 400 ppm, more than 0.1 ppm and less than 300 ppm, more than 0.1 ppm and less than 200 ppm, or more than 0.1 ppm and less than 100 ppm.

In an embodiment, the feed allulose syrup comprises sulfur dioxide in an amount of from 0.1 to 20 ppm. In an embodiment, the feed allulose syrup comprises sulfur dioxide in an amount of from 1 to 15 ppm. In an embodiment, the feed allulose syrup comprises less than 10 parts per billion of isovaleraldehyde. In an embodiment, the feed allulose syrup comprises less than 2 parts per billion of 2-aminoacetophenone. In an embodiment, the feed allulose syrup further comprises one or more additives. In an embodiment, the one or more additives may include an additive. In an embodiment, the one or more additives may include an anti-oxidant. In an embodiment, the one or more additives may include a buffer. The incorporation of a buffer in the feed allulose syrup maintains the pH of the feed allulose syrup within the desired range for a longer period. In an embodiment, additives are included at around 0.01-2.0% by weight based on the total weight of the feed allulose syrup. In an embodiment, the additive may be selected from the group consisting of ascorbic acid and salts thereof; isoascorbic acid (erythorbate) and salts thereof; citric acid and salts thereof; acetic acid and salts thereof; and salts of bisulfite and metabisulfite; and tocopherol acetate. In the case of salts, suitable salts include alkali metal salts, particularly sodium and potassium salts, and especially sodium salts. Specific examples of additives useful in the present invention include ascorbate, isoascorbate, sodium citrate, sodium acetate, tocopherol acetate and metabisulfite. In an embodiment, the stability enhancing additives are included at around 0.2% by weight based on the total weight of the feed allulose syrup in the case of ascorbic acid or salts thereof; isoascorbic acid (erythorbate) or salts thereof; citric acid or salts thereof; acetic acid or salts thereof; and tocopherol acetate. In an embodiment, the stability enhancing additives are included at around 0.02% by weight based on the total weight of the feed allulose syrup in the case of salts of bisulfite or metabisulfite.

The concentration of buffer included in the feed allulose syrup may be around 0.01-2.0% by weight based on the total weight of the feed allulose syrup. The concentration of buffer included in the feed allulose syrup may be around 0.2% by weight based on the total weight of the feed allulose syrup in the case of ascorbic acid or salts thereof; isoascorbic acid (erythorbate) or salts thereof; citric acid or salts thereof; acetic acid or salts thereof; and tocopherol acetate. The concentration of buffer included in the feed allulose syrup may be around 0.02% by weight based on the total weight of the feed allulose syrup in the case of salts of bisulfite or metabisulfite.

According to some embodiments, ranges for the dry solids in the allulose feed syrup include 60-80%, 70-80%, 71-78%, 71-73% or 76-78%. According to some embodiment, pH ranges of the allulose feed syrup are between 3.5 and 4.5 or between 3.8 and 4.2. The purity of the allulose in the feed allulose syrup may be greater than 95% allulose on a dry solids basis. The feed allulose syrup has a limited amount of the following compounds: less than 1000 ppm hydroxymethylfurfural (HMF); sulphur dioxide at a concentration of less than 20 parts per million; isovaleraldehyde at a measured concentration of less than 10 parts per billion; and 2-aminoacetophenone at a concentration of less than 2 parts per billion. Optionally, the feed allulose syrup can have any of the following compounds alone or in combination thereof: a stability enhancing ingredient including one or more of: 1) ascorbic acid or salts thereof, 2) isoascorbic acid (erythorbate) or salts thereof, 3) citric acid or salts thereof, 4) acetic acid or salts thereof, 5) salts of bisulfite or metabisulfite, and/or 6) tocopherol acetate. The feed allulose syrup may have a concentration of greater than 90% (e.g. greater than 95%).

The purity of the allulose syrup may vary, but typically it will be desirable for allulose to constitute the majority, by weight, of the non-volatile substances present in the allulose syrup. Accordingly, the allulose purity of the syrup may be, in various embodiments of the invention, at least 60% by weight, at least 65% by weight, at least 70% by weight, at least 75% by weight, at least 80% by weight, at least 85% by weight or at least 90% by weight, or at least 95% by weight or at least 96, 97, 98, or at least 99% by weight, or 100% by weight. The term "allulose purity" as used herein with respect to an allulose syrup means the percent by weight of allulose in the syrup, based on the total weight of dry solids in the syrup.

Seed Crystals of Allulose

The present invention employs seed crystals of allulose to help promote the initiation of crystallization of additional allulose from solution (e.g., the formation of solid crystals containing allulose that had previously been in solution in an allulose syrup, mother liquor or the like). In certain embodiments, the allulose seed crystals are in dry form (for example, dry crystals of allulose recovered from a previously performed crystallization) and/or in the form of a heel, such as a portion of a massecuite comprised of allulose crystals and a mother liquor. The precise amount of allulose seed crystals is not believed to be particularly critical, but may, for example, be employed in a quantity representing from about 0.1 to about 5% of the total amount of allulose present in a crystallization vessel or crystallization zone, as will be described in more detail subsequently.

Generally speaking, allulose seed crystals of relatively high purity are preferred for use; for example, the allulose seed crystals may have an allulose purity of at least 90%, at least 95% or at least 99% by weight, in various embodiments of the invention. The term "allulose purity" as used herein with respect to allulose crystals means the percent by weight of allulose in the crystals, based on the total weight of dry solids in the crystals.

According to some embodiments, the seed crystals have an average particle size of 75 microns or less. For example, the seed crystals may have an average particle size of from 5 to 250 microns. The average particle size may be measured by laser light scattering.

According to some embodiments, the seed crystals may be in dry form and may have an average particle size of 75 microns or less. According to some embodiments seed crystals may have an average particle size of from 5 to 250 microns. For example, the seed crystals may have an average particle size of at least 5, 25, 50, 75, 100, 125, 150, 175, or at least 250 microns. According to some embodiments the seed crystals may have an average particle size of at most 250, 200, 175, 150, 125, or at most 100 microns.

Description of Various Exemplary Embodiments of Crystallization Processes

In one embodiment of the invention, batch crystallization of allulose may be performed in a jacketed vessel equipped with an agitator by dropping the temperature of the cooling medium (e.g., water or other heat transfer liquid) in the jacket to lower the massecuite temperature and thereby drive crystallization. The following series of steps may be performed:

1. The vessel is partially filled with a suitable allulose syrup.
2. The temperature of the cooling medium is set at a desired initial temperature.
3. The agitator is started and set at an RPM effective to provide a desired tip speed.
4. The temperature of the allulose syrup in the vessel is lowered to a desired temperature, by varying the temperature of the cooling medium as appropriate.
5. A desired amount of seed crystals (e.g., dry seed crystals) is added to the vessel (this addition may be performed prior to the time the allulose syrup reaches the temperature referenced in step 2).
6. Mix the seed crystals and the allulose syrup, using an appropriate agitator tip speed. The agitator tip speed may be selected to minimize or avoid breakage of the seed crystals as well as the allulose crystals subsequently formed during crystallization. In certain embodiments, the agitator tip speed is higher during the initial mixing of the seed crystals with the allulose syrup than it is during the subsequent crystallization step(s).

7. The temperature of the allulose syrup/seed crystal admixture is then lowered to a desired temperature effective to achieve crystallization of a portion of the allulose dissolved in the allulose syrup. This temperature will vary, depending upon, for example, the concentration of allulose in the syrup, but typically will be not greater than about 40° C. and not less than about 0° C.

8. Crystallization is permitted to continue, with a suitable degree of agitation, until a desired yield of allulose crystals is achieved (this may be checked by periodically withdrawing a sample from the vessel and measuring the dry solids content of the mother liquor).

9. To achieve the desired yield of allulose crystals, the temperature of the massecuite may continue to be lowered, either continuously or in one or more stages.

10. Once the desired yield of allulose crystals is met, the massecuite is combined with an additional portion of allulose syrup (filling the vessel, for example). Steps 7-9 are then repeated.

11. Once the desired yield of allulose crystals is achieved following the introduction of the additional portion of allulose syrup into the vessel, a portion (e.g., approximately one-quarter to three-quarters) of the massecuite is removed from the vessel, with the remaining portion of the massecuite being retained in the vessel to serve as a source of seed crystals for a subsequent batch of massecuite. In this way, multiple batches of massecuite may be prepared.

12. The portion(s) of the massecuite withdrawn from the vessel may be subjected to one or more desired processing steps, such as separating the allulose crystals from the mother liquor by one or more physical separation methods selected from the group consisting of centrifugation, filtration, decantation, membrane separation and combinations thereof and then washing and/or drying the separated allulose crystals.

In another embodiment of the invention, the crystallization may be conducted in a continuous manner involving a plurality of stages (e.g., three or four stages). Such a process may be carried out using a system as illustrated in schematic form in FIG. 1 and as further explained as follows.

An allulose syrup of suitable purity is introduced through line 1 to evaporator 2, wherein the dry solids content of the syrup is increased to the desired level. The allulose syrup is then pumped (utilizing pump 3) through line 4 into allulose syrup feed hold-up tank 5. From tank 5, the allulose syrup is pumped (using pump 6) via line 7 and introduced into heat exchanger 8, wherein the temperature of the allulose syrup is adjusted to a desired value prior to being fed via line 9 to mix tank 10. In mix tank 10, the allulose syrup is combined, using vigorous mixing, with massecuite from crystallization zone 22, which is fed to mix tank 10 using line 25. An admixture of allulose syrup and massecuite (which serves as a source of seed crystals) is withdrawn from mix tank 10 and introduced into crystallization zone 12. Crystallization zone 12 may be within a suitable tank or other vessel equipped with an agitator. Any agitator of the type known in the art may be used; in particular, the agitator may be any of the types of mechanical devices recognized as being useful in agitating solution/seed crystal mixtures in a crystallization process may be utilized. In one embodiment, the agitator in the crystallization zone can bring about its agitating effect horizontally but not vertically. In order to prevent or reduce turbulent flow and destruction/breakage of the crystals formed during crystallization, the agitation can be preferably carried out at a low speed. The agitator may be configured and operated so as to prevent crystals of allulose from adhering to the wall(s) and/or the bottom of a vessel constituting crystallization zone 12. According to one aspect of the invention, the admixture of allulose syrup and massecuite is not subjected to concentration within crystallization zone 12. The allulose syrup/massecuite admixture may move through crystallization zone 12 in a plug flow manner, with the tip speed of the agitator being adjusted as appropriate to promote crystallization of allulose dissolved in the liquid phase of the admixture and to generate allulose crystals of the desired size and shape. In one embodiment, the process parameters are controlled such that the allulose syrup/massecuite admixture is passed, in a descending continuous flow, through a vessel comprising crystallization zone 12. The flow rate of the admixture through crystallization zone 12 and thus the residence time of the admixture in crystallization zone 12 are controlled such that the admixture exiting from crystallization zone 12 via line 14 has a desired content of allulose crystals (i.e., the desired yield of allulose crystals is achieved by the time the admixture is withdrawn from crystallization zone 12). In one embodiment, the temperature of the allulose syrup/massecuite admixture remains constant or essentially constant as the admixture passes through crystallization zone 12. For example, the temperature of the admixture may be controlled such that the admixture temperature at the point of introduction into crystallization zone 12 differs by no more than 5° C., no more than 4° C., no more than 3° C., no more than 2° C. or no more than 1° C. from the temperature of the admixture at the point where it exits or is withdrawn from crystallization zone 12.

The massecuite obtained from crystallization zone 12 is further cooled using heat exchanger 15 to a desired temperature (which may be, for example, about 1° C. to about 10° C. lower than the temperature of the massecuite as it exits from crystallization zone 12) and introduced into crystallization zone 17, via line 16. According to one embodiment of the invention, the massecuite obtained from crystallization zone 12 is not subjected to concentration before or after being introduced into crystallization zone 17. Crystallization zone 17 may be within a suitable tank or other vessel equipped with an agitator. The massecuite may move through crystallization zone 17 in a plug flow manner, with the tip speed of the agitator being adjusted as appropriate to promote crystallization of allulose still dissolved in the liquid phase (mother liquor) of the massecuite. The flow rate of the massecuite through crystallization zone 17 and thus the residence time of the admixture in crystallization zone 17 are controlled such that the admixture exiting from crystallization zone 17 via line 18 has a desired content of allulose crystals (i.e., the desired yield of allulose crystals is achieved by the time the massecuite is withdrawn from crystallization zone 17), with the desired content of allulose crystals being higher than that of the massecuite withdrawn from crystallization zone 12. The massecuite in crystallization zone 17 is not subjected to concentration, according to one embodiment of the invention.

The massecuite obtained from crystallization zone 17 is further cooled using heat exchanger 20 to a desired temperature (which may be, for example, about 1° C. to about 10° C. lower than the temperature of the massecuite as it exits from crystallization zone 17) and introduced into crystallization zone 22, via line 21. According to one embodiment of the invention, the massecuite obtained from crystallization zone 17 is not subjected to concentration before or after being introduced into crystallization zone 22. Crystallization zone 22 may be within a suitable tank or other vessel equipped with an agitator. The massecuite may move through crystallization zone 22 in a plug flow manner, with the tip speed of the agitator being adjusted as appropriate to promote crystallization of allulose still dissolved in the liquid phase (mother liquor) of the massecuite. The flow rate of the massecuite through crystallization zone 22 and thus the residence time of the admixture in crystallization zone 22 are controlled such that the admixture exiting from crystallization zone 22 via line 23 has a desired content of allulose crystals (i.e., the desired yield of allulose crystals is achieved by the time the massecuite is withdrawn from crystallization zone 22), with the desired content of allulose crystals being higher than that of the massecuite withdrawn from crystallization zone 17. The massecuite in crystallization zone 22 is not subjected to concentration, according to one embodiment of the invention.

If so desired, one or more additional crystallization zones (not illustrated) may be introduced, which is or are operated in a manner similar to that of crystallization zones 12, 17 and 22, wherein the massecuite exiting crystallization zone 22 is subjected to further cooling and crystallization. According to certain embodiments of the invention, such further processing is carried out without any concentration of the massecuite.

Once a massecuite having the desired final target yield of allulose crystals has been produced, a portion of it may be recycled and utilized as a source of seed crystals as previously mentioned (being conveyed via line 25 to mix tank 10) and the remaining portion may be passed through heat exchanger 27 and fed via line 28 to massecuite hold-up tank 29. The massecuite from massecuite hold-up tank 29 may be subjected to a separation of the allulose crystals from the mother liquor using centrifuge 30, with the resulting cake of allulose crystals then being washed before being dried in rotary dryer 31.

Figure 2:
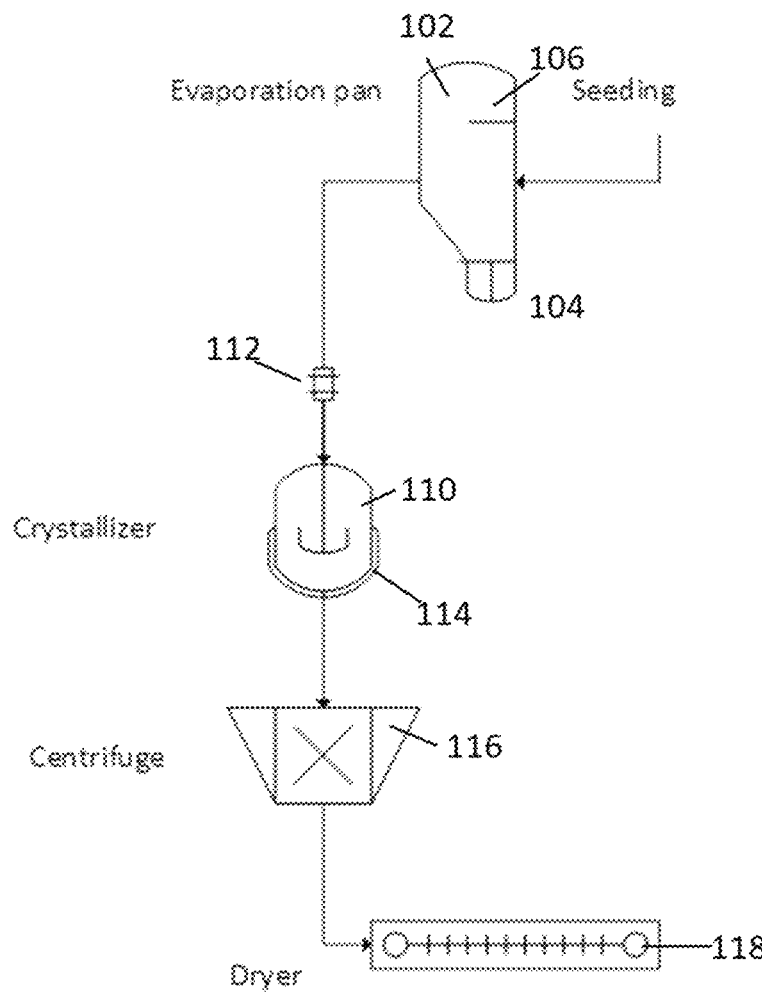
FIG. 2 illustrates in schematic form a crystallization system and process in accordance with another embodiment of the invention.

In another embodiment of the invention, shown in FIG. 2, the crystallization of allulose from a feed syrup may be performed in an evaporator 102 in contact with a suitable heating medium 104 and equipped with a vacuum 106. The vacuum 106 may be configured and arranged to pull a vacuum on a feed syrup. The evaporator 102 may be constructed and arranged to heat or cool a feed syrup, either alone or in combination with the vacuum 106, in order to reduce the amount of liquid in the feed syrup and thereby increase the solids content in the feed syrup. The evaporator 102 may also be configured and arranged to accept seed crystals. According to an embodiment, the evaporator 102 may be in fluid communication with a crystallizer unit 110 as shown in FIG. 2. According to another embodiment, the crystallizer unit 110 may be a separate unit. According to another embodiment, a valve and/or pump 112 may be interposed between the evaporator 106 and the crystallizer unit 110, as shown in FIG. 2. The crystallizer unit 110 may be configured and arranged to cool a massecuite. According to some embodiments, the crystallizer unit 116 may be a batch unit or may be a continuous crystallizer. The crystallizer unit 110 may be equipped with agitators. Any agitator of the type known in the art may be used; in particular, the agitator may be any of the types of mechanical devices recognized as being useful in agitating solution/seed crystal mixtures in a crystallization process may be utilized. In one embodiment, the agitator in the crystallization unit 110 can bring about its agitating effect horizontally but not vertically. In order to prevent or reduce turbulent flow and destruction/breakage of the crystals formed during crystallization, the agitation can be preferably carried out at a low speed. The agitator may be configured and operated so as to prevent crystals of allulose from adhering to the wall(s) and/or the bottom of a vessel constituting crystallization. As may be seen in FIG. 2, the crystallizer unit 110 may be in fluid communication with a centrifuge 116, or the centrifuge 116 may be a separate unit. The centrifuge 114 as shown in FIG. 2 may be in communication with a dryer 118. The centrifuge 118 may be configured and arranged to separate the allulose crystals from the bulk of the mother liquor in the massecuite. According to an embodiment, the allulose crystals may be washed before being passed to the dryer 118. According to an embodiment, the dryer 118 may be a separate unit. In some embodiments the dryer 118 is configured and arranged to remove moisture from the allulose crystals. The dryer may be a rotary dryer, for example.

The following series of steps may be performed in the equipment shown in FIG. 2:

1. The evaporator 102 is filled with a suitable feed allulose syrup.
2. The temperature of the heating medium 104 is set at a desired initial temperature. This temperature may from 35° C. to 55° C., or from 45° C. to 50° C.
3. The vacuum 106 in the evaporator 102 is set at a desired level. The pressure in the evaporator 102 is therefore less than ambient.
4. During the process of evaporation, the evaporator 102 is seeded with a desired amount of crystalline allulose when the syrup in the evaporator reaches a desired dry solids weight %. The amount of seed crystal may be from 0.0001% to as much as 5% by weight based on a weight of the syrup in the evaporator unit. According to some embodiments, the amount of seed crystal may be from 0.0001 to 5%, or from 0.05 to 0.5%, or from 0.2 to 1.2% by weight, based on a weight of the syrup in evaporator unit 102.
5. Evaporation in the evaporator 102 is continued until a massecuite forms, wherein the desired amount of crystal count in the massecuite is achieved in the evaporator. The massecuite includes a mother liquor and allulose crystals. The mother liquor may be supersaturated. According to some embodiment the mother liquor may be 1.01, 1.02, 1.05, 1.1, 1.15, 1.2, 1.25, 1.3, 1.35, 1.4, 1.45, or 1.5 supersaturated. According to some embodiments the amount of crystal may be from 20 to 90%, from 40 to 80%, or from 50 to 75%, or from 60 to 70% by weight of the massecuite in the evaporator 102.
6. Optionally, the temperature of the massecuite in the evaporator 102 may be reduced to increase supersaturation of the massecuite and the reduced temperature may be held for a desired time to further complete crystallization and obtain additional crystal yield. The temperature may be dropped by 2, 5, 10, 15 or 20° C. from the initial temperature, according to some embodiments. According to some embodiments, the supersaturation of the mother liquor may be 1.1, 1.15, 1.2, 1.25, 1.3, 1.35, 1.4, 1.45, or 1.5 supersaturated.
7. The massecuite can then be dropped or pumped (by opening or using valve and/or pump 112) or placed into the cooling crystallizer unit 110.
8. The cooling crystallizer unit 110 may be batch or continuous.
9. The temperature of the cooling medium 114 of the cooling crystallizer unit 110 is set at a desired initial temperature. According to some embodiments, this initial temperature may be the same or less than either the initial or cooled temperature of the evaporator 102. According to some embodiments, the temperature of the massecuite in the crystallizer unit 110 may vary, depending upon, for example, the concentration of allulose in the syrup, but typically will be not greater than about 40° C. and not less than about 0° C. According to some embodiments, the temperature of the massecuite in the crystallizer unit 110 may be not less than 15° C., or not less than 10° C.

10. The agitator in the cooling crystallizer unit 110 is started and set at an RPM effective to provide a desired tip speed. According to some embodiments, the tip speed may be from 0.2 to 2 m/s 11. The temperature of the massecuite in the crystallizer unit 110 is lowered to a desired temperature, by varying the temperature of the cooling medium 114 as appropriate. This massecuite temperature will vary, depending upon, for example, the concentration of allulose in the mother liquor of the massecuite, but typically will be not greater than about 40° C. and not less than about 0° C. According to some embodiments, the temperature of the massecuite may be from 10° C. to 35° C., or from 20° C. to 30° C.

12. Crystallization is permitted to continue, with a suitable degree of agitation, until a desired yield of allulose crystals is achieved. The yield may be checked by periodically withdrawing a sample from the crystallizer unit 110 and measuring the dry solids content of the mother liquor.

13. To achieve the desired yield of allulose crystals, the temperature of the massecuite in the crystallizer unit 110 may continue to be lowered, either continuously or in one or more stages.

14. Once the desired yield of allulose crystals is achieved, the massecuite may be subjected to one or more desired processing steps, such as separating the allulose crystals from the mother liquor by one or more physical separation such as centrifugation, filtration, decantation, membrane separation, or combinations thereof and then washing and/or drying the separated allulose crystals. As shown in FIG. 2, the massecuite in the crystallizer unit 110 may be separated into allulose crystals and the mother liquor using a centrifuge 116. The allulose crystals may be washed in the centrifuge 116, or in a separate unit. The allulose crystals from the centrifuge 116 are then sent to a dryer 118, where the remaining moisture is removed.

Thus, according to an embodiment, a method for producing allulose crystals is provided. The method comprises the following steps.

Evaporating a feed allulose syrup at a first sub-ambient pressure and a first temperature to produce a first supersaturated allulose syrup having an allulose syrup target saturation. According to some embodiments, the feed syrup may already be supersaturated and thus this step serves to further saturate the allulose syrup. The concentration of allulose in the supersaturated syrup may be conveniently measured by measuring refractive index. Then seed crystals are introduced to the first supersaturated allulose syrup and the allulose is allowed to crystallize to produce a first massecuite comprising allulose crystals and a first supersaturated mother liquor having a first target mother liquor saturation. This target mother liquor saturation is higher than the allulose syrup target saturation. The first massecuite is evaporated at the first sub-ambient pressure and the first temperature to produce a second massecuite comprising allulose crystals and a second supersaturated mother liquor having a second mother liquor target saturation which is lower than the first mother liquor target saturation. The first sub-ambient pressure is increased to second sub-ambient pressure and the second massecuite is cooled to a second temperature to produce a third massecuite comprising allulose crystals and a third supersaturated mother liquor having a third mother liquor target saturation. At this point, the third massecuite is held at the second sub-ambient pressure and the second temperature for a period of time to produce a fourth massecuite comprising fourth allulose crystals and a fourth mother liquor having a fourth target mother liquor saturation. The period of time may be from 10 minutes to an hour to 2 hours, or 3 hours or 4 hours or up to 6 hours. Then, the vacuum is released and the pressure increases to ambient. This fourth massecuite is cooled to a third temperature at a cooling rate to produce a fifth massecuite comprising fifth allulose crystals and a fifth supersaturated mother liquor having a fifth target mother liquor saturation. The cooling rate may be from 0.5° C. per hour to 1.25° C. per hour or from 0.1° C. per hour to 0.6° C. per hour. Upon reaching the third temperature, the fifth massecuite is allowed to crystallize for a crystallization time to produce a product massecuite comprising product allulose crystals at a target yield and a product mother liquor, the product mother liquor having a target product mother liquor supersaturation. The crystallization time may be from 10 minutes to an hour to 2 hours, or 3 hours or 4 hours or up to 6 hours or longer as necessary in order to attain the target yield. Then the product allulose crystals are separated from the product supersaturated mother liquor to provide allulose crystals at the target yield.

Generally speaking, it will be desirable to control the crystallization conditions such that the final massecuite (i.e., the massecuite from which allulose crystals will be recovered, involving separation from the mother liquor component of the massecuite) does not have an overly high content of allulose crystals, since a high allulose crystal concentration may tend to result in a massecuite which has a high viscosity and which is consequently difficult to further process. Accordingly, in various embodiments of the invention, the yield of allulose crystals in the final massecuite is not more than 90%, not more than 85%, not more than 80%, not more than 75%, not more than 70%, not more than 65%, not more than 60%, not more than 55%, not more than 50% or not more than 45%. At the same time, it is desirable for the allulose crystal yield which is achieved in the final massecuite to be sufficiently high so as to reduce production costs. Thus, in various embodiments, the yield of allulose crystals in the final massecuite is at least 20%, at least 25%, at least 30%, at least 35% or at least 40%.

The mother liquor(s) separated from allulose crystals in accordance with various embodiments of the invention may be further processed and/or used in different ways. For example, a mother liquor recovered from a separation step may be simply used as is (e.g., in solution or syrup form) as a source of allulose in preparing or formulating a consumable product. If so desired, the mother liquor may be subjected to one or more processing steps such as concentration (evaporation) and/or treatment to remove impurities (using adsorbents or the like). In still other embodiments, a recovered mother liquor may be recycled back into a crystallization process of the type described herein, thus serving as a source (in whole or in part) of an allulose syrup starting material. Prior to such recycling, the mother liquor may be subjected to one or more processing steps such as concentration and/or purification.

Further Processing of Allulose Crystals

In various embodiments of the present invention, the method may comprise one or more additional steps wherein the allulose crystals present in a massecuite, following separation from the mother liquor portion of the massecuite by centrifugation, filtration, decantation, membrane separation or other such physical separation method, are subjected to further processing. For example, allulose crystals as separated from a mother liquor typically have some amount of the mother liquor on the outer surface to the crystals. Because the mother liquor generally contains some amount of impurities (substances other than allulose), the purity of the recovered crystals may be improved by subjecting the separated allulose crystals to one or more washing steps, wherein one or more volumes of a suitable liquid are used to wash the crystals. The washing step(s) may be performed in any suitable manner using techniques known in the art, such as passing the washing liquid through a bed of the allulose crystals or by slurrying the separated allulose crystals in a volume of the washing liquid and then subjecting the slurry to a physical separation step such as centrifugation, decantation, membrane separation and/or filtration to recover washed allulose crystals from the washing liquid. Any suitable washing liquid may be utilized, such as water, an organic solvent (e.g., an alcohol, such as ethanol), a blend of water and one or more organic solvents, a blend of two or more organic solvents, and/or an aqueous solution comprised of at least one carbohydrate such as allulose. In one embodiment, the allulose crystals are washed with an allulose syrup or even a recovered mother liquor having a purity (with respect to allulose) that is higher than the purity of the residual mother liquor initially present in the crystals to be washed.

The allulose crystals separated from the mother liquor of a massecuite may be subjected to a drying step to lower the moisture content of the crystals. The drying step may, for example, be carried out subsequent to a washing step or series of washing steps. The drying of the crystals may be performed in a fluidized bed dryer, a rotary dryer, a vacuum dryer or other such apparatus. For example, in the drying step, the allulose crystals may be dried using an air temperature of up to approximately 100° C., preferably no greater than 80° C., over a period of about 20 minutes to about 24 hours, more preferably about 20 minutes to about 6 hours.

The present invention is capable of producing dry, relatively large, free-flowing crystals of allulose at a lower manufacturing cost (due to better utilization of equipment), as compared to previously known allulose crystallization processes. Such larger crystals have a better appearance than small allulose crystals, which often appear powdery or fluffy. Larger crystals have fewer fines, which in turn leads to lower dusting. Fines (i.e., small crystals) can pack into the spaces between large crystals, possibly resulting in poor flow characteristics as well as caking issues. Additionally, small crystals of allulose have greater surface area as compared to large crystals; this leads to faster moisture sorption, which can also contribute to caking. Dry, free-flowing allulose crystals of the type which can be produced economically using the present invention permit handling by a customer (e.g., a food manufacturer) without the need for special handling equipment.

Processes in accordance with the present invention are capable, for example, of producing an allulose crystal product having an average particle size of at least 100 microns, at least 150 microns, at least 200 microns, or at least 250 microns or even larger (e.g., 250 to 350 microns), in various embodiments of the invention. Average particle size may be determined using a laser diffraction particle size analyzer, such as the LS 13 320 model manufactured by Beckman Coulter. According to certain aspects of the invention, less than 25% of the allulose crystal product obtained is smaller than 75 microns in size. According to some embodiments the average particle size is at least 275 microns, at least 300 microns, at least 325 microns, at least 350 microns, at least 375 microns, at least 400 microns, at least 425 microns, at least 450 microns, at least 475 microns or up to 500 microns in size.

Figure 3:
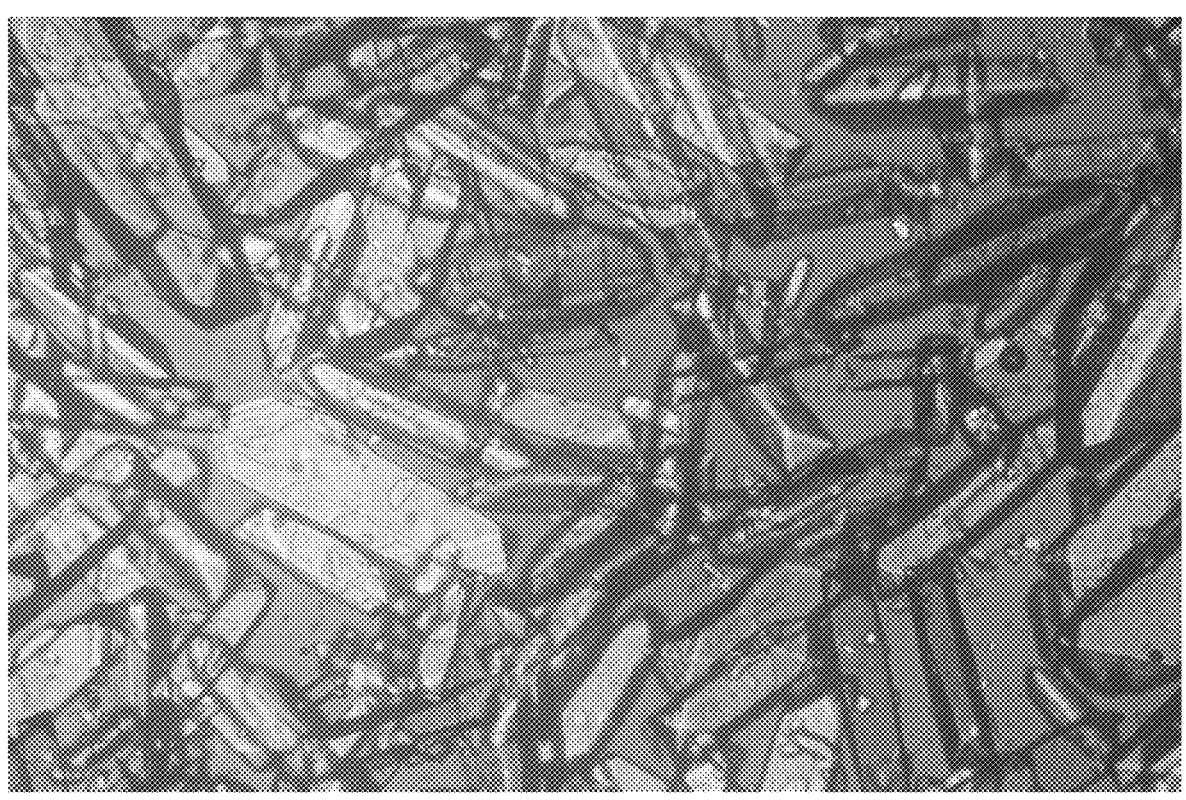
FIG. 3 is a microscopic image of a massecuite containing allulose crystals which has been produced in accordance with an embodiment of the invention.

The present invention can be practiced to obtain allulose crystals having a preferred morphology wherein the allulose crystal has a well-defined three-dimensional shape, rather than the shape of a needle or a flat sheet. FIG. 3 is a microphotographic image of allulose crystals in a massecuite which have such a preferred morphology. The crystals may have a triangular shaped cross-section.

Allulose crystals produced in accordance with at least certain embodiments of the invention may advantageously have, for example, a bulk density greater than 30 lb/ft$^3$ and more preferably greater than 35 lb/ft$^3$. According to some embodiments, the bulk density may be at least 20, 25, 30, 35, 40, 45, 50, 55 or at least 60 lb/ft$^3$.

Uses for Allulose Crystals

Allulose crystals produced by the method of the present invention may be used in a product for human and/or animal consumption. Such use is particularly advantageous in products having a low water content. In some embodiments, the product may be a food product, a beverage product, a pharmaceutical product, a nutritional product, a sports product, or a cosmetic product. For example, when the product is a food product, the food product can be selected from the group consisting of a confectionary product (including a chocolate product), a dessert product, a cereal product, baked goods, frozen dairy products (e.g., ice cream), meats, dairy products (e.g., yogurt), condiments, snack bars, energy bars, nutrition bars, soups, dressings, mixes, prepared foods, baby foods, diet preparations, syrups, food coatings, dried fruit, sauces, gravies, and jams/jellies. In some embodiments, the food product may comprise allulose crystals produced by the method of the present invention in the form of a coating or frosting formed on the surface of the product. Alternatively, when the product is a beverage product, the beverage product can be selected from the group consisting of a carbonated beverage, a non-carbonated beverage, fruit-flavored beverage, fruit juice, tea, milk, coffee, and the like. The food product containing allulose crystals produced in accordance with the invention may also be a tabletop sweetener.

Allulose crystals produced in accordance with the present invention may be used in combination with one or more other food or beverage ingredients, including any of the food and beverage ingredients known in the art. Such additional food and beverage ingredients include, but are not limited to, flavorants, colorants, sweeteners other than allulose including other carbohydrates such as sucrose, fructose, allose, tagatose and other rare carbohydrates, synthetic high potency sweeteners such as sucralose, acesulfame K, saccharin, aspartame and the like, natural high potency sweeteners such as stevia and monk fruit extract sweeteners and the terpene glycosides present therein, such as steviol glycosides and mogrosides including, but not limited to, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M (also known as rebaudioside X), rebaudioside N, rebaudioside O, stevioside, steviolmonoside, steviolbioside, dulcoside A, dulcoside B, rubusoside, glycosylated steviol glycosides, enzyme-modified steviol glycosides, mogroside II A, mogroside II B, 7-oxo-mogroside II E, 11-oxomogroside A, mogroside III A2, 11-deoxymogroside III, 11-oxymogroside IV A, 7-oxomogroside V, 11-oxomogroside V, mogroside V, mogroside VI and the like and combinations thereof), dietary fibers (including soluble dietary fibers such as soluble corn fiber and polydextrose), acidulants, water, and the like. The allulose crystals may be admixed or blended with such other ingredients in dry form. In other embodiments, the allulose crystals may be coated with one or more other ingredients; for example, a solution containing one or more other ingredients (such as a high potency sweetener, combination of high potency sweeteners, and/or one or more other carbohydrates), may be applied to the allulose crystals by spraying or other such procedure and then dried.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein. In some embodiments, the invention herein can be construed as excluding any element or process step that does not materially affect the basic and novel characteristics of the composition or process. Additionally, in some embodiments, the invention can be construed as excluding any element or process step not specified herein. Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

Allulose syrup, Dolcia Prima® LS (Tate & Lyle), may be introduced in an evaporative pan and evaporated under vacuum at 100-120° F. to 87-88% dry solids content. During evaporation, when the saturation of the syrup reaches around 1.13, i.e. the syrup is 13% beyond 100% saturation. Saturation of the syrup may be seeded with ultrafine milled crystalline allulose seed. Particle size of the milled seed may vary although a preferred particle size distribution of the final product is less than 75 micron average particle size. Particle size of seed can vary from 5 micron to 250 micron. Amount of milled seed can be as little as 0.0001% to as much as 5%. The evaporation may be continued until saturation of the mother liquor is 1.05 or less.

Reduce the temperature and draw vacuum on the evaporator until the temperature is 10° F. (° C.) lower and hold for approximately 1-4 hours until the saturation of the mother liquor is 1.05 or less again.

Drop the crystalline massecuite into a cooling crystallizer. Crystallize the batch by cooling the massecuite to a saturation of 1.2 to 1.3 and let it crystallize to a saturation of down to 1.05 to 1.16. Repeat the cooling steps until a yield of 50 to 60% of the allulose crystals is achieved, or until the massecuite gets too thick to handle. For example, the massecuite may have viscosity of about 40,000 cP at this point. The massecuite may have a viscosity of 80,000 cP or less at this point. At this point the refractive index of mother liquor is 1.4695 or less.

The temperature and details of the allulose syrup during the above process may be shown as depicted in Table 1, along with wt % yield of the allulose. The yield is calculated as: (Mass of allulose crystallized from the syrup)/(Mass of allulose in the feed syrup)×100.

TABLE 1

| Massecuite temperature ° F. (° C.) | Refractive Index of Mother Liquor | Mother Liquor Allulose content, dry solids, based on refractive index | Saturation of mother liquor in massecuite | Wt % allulose yield |
|---|---|---|---|---|
| 110 (43.3) (evaporation)* | 1.4923 | 87.04 | 1.24 | 0.0% |
| 110 (43.3) (evaporation) | 1.4870 | 85.00 | 1.04 | 16.5% |
| 100 (37.8) (evaporation) | 1.4870 | 85.00 | 1.21 | 16.5% |
| 100 (37.8) (evaporation) | 1.4817 | 82.91 | 1.02 | 29.3% |
| 90 (32.2) (cooling) | 1.4817 | 82.91 | 1.19 | 29.3% |
| 90 (32.2) (cooling) | 1.4792 | 81.90 | 1.11 | 34.4% |
| 85 (29.4) (cooling) | 1.4792 | 81.90 | 1.20 | 34.4% |
| 85 (29.4) (cooling) | 1.4767 | 80.89 | 1.11 | 39.0% |
| 80 (26.7) (cooling) | 1.4767 | 80.89 | 1.20 | 39.0% |
| 80 (26.7) (cooling) | 1.4742 | 79.86 | 1.12 | 43.2% |
| 75 (23.9) (cooling) | 1.4742 | 79.86 | 1.20 | 43.2% |
| 75 (23.9) (cooling) | 1.4717 | 78.83 | 1.12 | 47.0% |
| 70 (21.1) (cooling) | 1.4717 | 78.83 | 1.20 | 47.0% |
| 70 (21.1) (cooling) | 1.4692 | 77.78 | 1.12 | 50.5% |

*Seed when saturation reaches 1.13.

What is claimed is:

1. A method for producing allulose crystals, wherein the method comprises:

a) evaporating a feed allulose syrup at a first sub-ambient pressure and a first temperature to produce a first supersaturated allulose syrup having an allulose syrup target saturation;

b) introducing seed crystals to the first supersaturated allulose syrup and allowing the allulose to crystallize to produce a first massecuite comprising first allulose crystals and a first supersaturated mother liquor having a first target mother liquor saturation higher than the allulose syrup target saturation;

c) evaporating the first massecuite at the first sub-ambient pressure and the first temperature to produce a second massecuite comprising second allulose crystals and a second supersaturated mother liquor having a second mother liquor target saturation lower than the first mother liquor target saturation;

d) increasing the first sub-ambient pressure to a second sub-ambient pressure and cooling the second massecuite to a second temperature to produce a third massecuite comprising third allulose crystals and a third supersaturated mother liquor having a third mother liquor target saturation;

e) holding the third massecuite at the second sub-ambient pressure and the second temperature for a period of time to produce a fourth massecuite comprising fourth allulose crystals and a fourth mother liquor having a fourth target mother liquor saturation;

f) increasing the pressure to ambient and cooling the fourth massecuite to a third temperature at a cooling rate to produce a fifth massecuite comprising fifth allulose crystals and a fifth supersaturated mother liquor having a fifth target mother liquor saturation;

g) allowing the fifth massecuite to crystallize for a crystallization time to produce a product massecuite comprising product allulose crystals at a target yield and a product mother liquor, the product mother liquor having a target product mother liquor supersaturation; and h) separating the product allulose crystals from the product supersaturated mother liquor to provide the product allulose crystals at the target yield, wherein temperatures for the evaporating and cooling are effectively controlled to reliably obtain the target yield.

2. The method of claim 1, wherein the target yield of the product allulose crystals is 40% or more of the feed allulose syrup.

3. The method of claim 1, wherein the feed allulose syrup has a total dry solids content of from 50% to 80% by weight.

4. The method of claim 1, wherein the allulose in the feed allulose syrup is at least 80% pure on a dry solids basis by weight.

5. The method of claim 1, wherein the pH of the feed allulose syrup is from 2.5 to 6.0.

6. The method of claim 1, wherein the feed allulose syrup is at least 95% pure on a dry solids basis by weight.

7. The method of claim 1, wherein the feed allulose syrup is at least 98% pure on a dry solids basis by weight.

8. The method of claim 1, wherein the seed crystals comprise from 0.0001% to 5% by weight of the feed allulose syrup.

9. The method of claim 1, wherein the seed crystals have an average particle size of 75 microns or less.

10. The method of claim 1, wherein the seed crystals have an average particle size of from 5 to 250 microns.

11. The method of claim 1, wherein the first temperature is from 35 to 50° C.

12. The method of claim 1, wherein the first target mother liquor saturation is from 1.10 to 1.15.

13. The method of claim 1, wherein the first supersaturated mother liquor comprises from 85-90 wt % allulose on a dry solids basis.

14. The method of claim 1, wherein the second temperature is from 22 to 35° C.

15. The method of claim 1, wherein the second target mother liquor saturation is 1.05 supersaturated or less.

16. The method of claim 1, wherein the second supersaturated mother liquor comprises from 80 to 95 wt % allulose on a dry solids basis.

17. The method of claim 1, wherein the third temperature is from 20 to 25° C.

18. The method of claim 1, wherein the fourth target mother liquor saturation is from 1.1 to 1.2 supersaturated.

19. The method of claim 1, wherein the fifth target mother liquor saturation is from 1.05 to 1.2 supersaturated.

20. The method of claim 1, wherein the separating is carried out at least in part by one or more physical separation methods selected from the group consisting of centrifugation, filtration, decantation, membrane separation and combinations of distinct separation methods thereof.

21. The method of claim 1, wherein the product allulose crystals separated from the product mother liquor are further subjected to i) washing with at least one of water, an organic solvent, a blend of organic solvents, a blend of water and organic solvent(s) or an aqueous solution containing at least one carbohydrate; ii) drying; or a combination thereof.

22. Product allulose crystals, obtained in accordance with the method of claim 1.

23. A consumable product, comprising the product allulose crystals in accordance with claim 1 and at least one additional ingredient other than allulose crystals.

24. A method of making a consumable product, comprising combining the product allulose crystals prepared in accordance with claim 1 and at least one additional ingredient other than the product allulose crystals.

25. A mother liquor, comprising the product supersaturated mother liquor obtained in accordance with the method of claim 1.

26. A mother liquor, comprising the product supersaturated mother liquor obtained in accordance with the method of claim 1, wherein the mother liquor is suitable for use as a product consumable by humans or animals or as an ingredient in a formulated product consumable by humans or animals.

* * * * *